United States Patent [19]

Shore et al.

[11] 4,338,289

[45] Jul. 6, 1982

[54] PREPARATION OF DECABORANE (14) THROUGH HYDRIDE ION ABSTRACTION REACTIONS

[75] Inventors: Sheldon G. Shore, Columbus; Mark A. Toft, Amlin, both of Ohio; Francis L. Himpsl, Matawan, N.J.

[73] Assignee: The United States of America as represented by the Secretary of the Army, Washington, D.C.

[21] Appl. No.: 291,713

[22] Filed: Aug. 10, 1981

[51] Int. Cl.$^3$ ............................................. C01B 35/18
[52] U.S. Cl. ........................................ 423/294; 568/3; 568/4
[58] Field of Search .................... 423/276, 294; 568/3, 568/4

[56] References Cited

U.S. PATENT DOCUMENTS 3,152,867 10/1964 Tyson .................................. 423/294
3,489,517 1/1970 Shore et al. ........................... 23/204
4,115,520 9/1978 Dunks et al. .......................... 423/287
4,115,521 9/1978 Dunks et al. .......................... 423/294

Primary Examiner—G. O. Peters
Attorney, Agent, or Firm—Nathan Edelberg; Robert P. Gibson; Jack W. Voigt

[57] ABSTRACT

Disclosed is a method for the preparation of decaborane-14($B_{10}H_{14}$) in high yields from $B_5H_9$ which involve three basic procedure steps as follows:

(1) conversion of $B_5H_9$ to a solid, $[N(CH_3)_4][B_9H_{14}]$, by reacting NaH in a tetrahydrofuran (THF) solution in the presence of $[N(CH_3)_4][Cl]$;

(2) performing a hydride abstraction on the solid after removal of THF by reacting, while stirring, a boron trihalide selected from $BBr_3$ and $BCl_3$ to form $B_{10}H_{14}$; and, (3) separating the $B_{10}H_{14}$ from the solid reaction mixture by a sublimation procedure.

4 Claims, 1 Drawing Figure

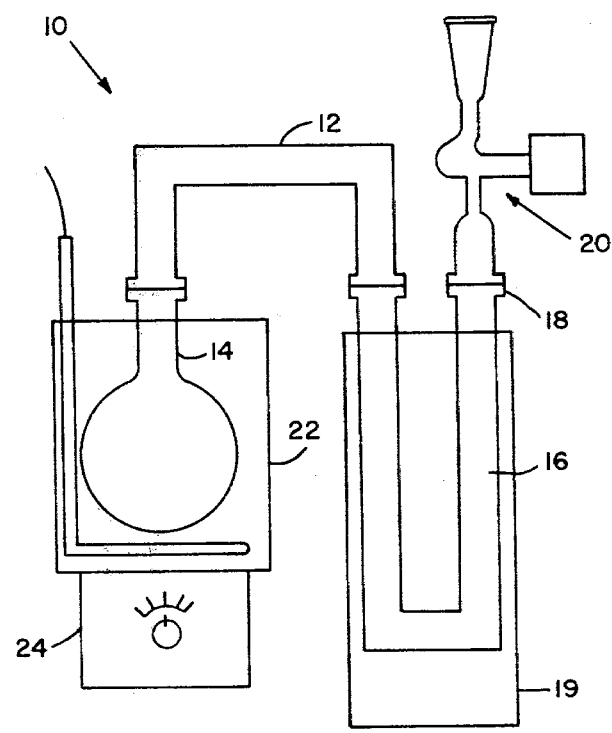

PREPARATION OF DECABORANE (14) THROUGH HYDRIDE ION ABSTRACTION REACTIONS

DEDICATORY CLAUSE

The invention described herein was made in the course of or under a contract or subcontract thereunder with the Government; therefore, the invention described herein may be manufactured, used, and licensed by or for the Government for governmental purposes without the payment to us of any royalties thereon.

BACKGROUND OF THE INVENTION

High performance solid propellant fueled rocket motors require burning rate catalysts to achieve fast burn rates. Presently, n-hexylcarborane (NHC) is considered to be one of the most suitable burning rate catalysts for solid propellant fuels. NHC production involves reacting 1-octyne with decaborane-14. The price and quantity limiting factor in the supply of NHC is the lack of an industrial process for synthesizing large quantities of decaborane inexpensively.

Thus, the key element in upgrading a weapon system to meet the desired level of performance for its propulsion subsystem is the use of the carborane burning rate modifier, NHC in the propellant. NHC, while extremely effective, is very costly, currently around $2,000/lb. The high cost is due chiefly to the cost in preparing a precursor, decaborane ($B_{10}H_{14}$), from diborane ($B_2H_6$).

The present production of decaborane-14 ($B_{10}H_{14}$) from $B_2H_6$ by pyrolysis methods lead to the excitation of all degrees of freedom of the reactant molecule. Both external (translational) and internal (electronic, vibrational, and rotational) degrees of freedom are usually in thermodynamic equilibrium. In addition to there being an unproductive waste of energy, reactions with equilibrium excited molecules characteristically proceed in the direction of breaking of the weakest bond, completing a considerable percent of back reactions, completing many side reactions, and producing polymers, many of which are not the desired product. The percent yield of the desired product is low since a number of boron polymers or undesirable products are formed. Also, separation of the desired product leads to complexities in the chemical engineering process for the usual commercial source method for $B_{10}H_{14}$.

A process which does not involve pyrolysis or producing decaborane-14 ($B_{10}H_{14}$) is disclosed in U.S. Pat. 3,489,517 by Shore et al. The general procedure for this process comprises reacting together any of the alkali metal (Li, Na, K)$B_5H_8$ salts (i.e., an alkali metal pentaborane-8) with diborane in an alkyl ether ($R_2O$) solvent including diethyl ether, glyme (1,2-dimethoxyethane) and diglyme[bis(2-methoxyethyl)ether]. Completion of the reaction is indicated when hydrogen evolution ceases. The desired decaborane-14 is recovered from the reaction mixture.

More recently, U.S. Pat. Nos. 4,115,520 and 4,115,521 issued to Dunks et al. on Sept. 19, 1978, disclose the process for preparation of compounds $MB_{11}H_{14}$ (wherein M is a monovalent cation) and the process for preparation of $B_{10}H_{14}$ by oxidation of the $B_{11}H_{14}^{(-)}$ ion of the compound $MB_{11}H_{14}$. These patents together provide disclosures for the preparation of $B_{10}H_{14}$ by nonpyrolytic methods.

The improvements provided by the nonpyrolytic processes by Shore et al and Dunks et al are recognized when compared with the pyrolytic processes of the earlier prior art. The yield of 25% based on the $B_5H_9$ used in the Shore et al process indicates that an improved method which is more direct and which provides a higher percent yield would be an advantageous advancement in the state-of-the art. Also, the Dunks et al process which employs a $B_{11}H_{14}^-$ ion must be carried out in a liquid medium which is unreactive toward the oxidants and the boron-containing reagents and products, and which facilitates contact of the $B_{11}H_{14}^-$ ion with the oxidatively active moiety of the oxidation agent. Again, one recognizes that this process which requires removal of one boron atom from $B_{11}H_{14}^-$ ion to produce $B_{10}H_{14}$ by oxidation in an aqueous medium could be improved by a method where the final reaction is conducted between all solid reactants to produce $B_{10}H_{14}$ in high yield by adding a single boron atom to an anionic starting material by a hydride ion abstraction procedure. The advantages of a method for the conversion of pentaborane-9 to decaborane-14 and the separation of decaborane-14 by a sublimation process from the solid reaction medium in which it is formed are readily recognized over a solvent process, particularly where water and non-polar organic media are required in the reaction and separation techniques.

A nonpyrolytic method for producing $B_{10}H_{14}$ from a starting material containing a greater number of boron atoms would be attractive, particularly, if the method is a simple method which results in good yields of $B_{10}H_{14}$.

A method for producing $B_{10}H_{14}$ from a starting material which is already available in quantity reserves would be particularly attractive in view of present day financial costs to produce $B_{10}H_{14}$ by pyrolysis methods.

An object of this invention is to provide a systematic approach to boron hydride syntheses wherein the syntheses relate to hydride ion abstraction from certain boron hydride anions to yield as one of the final products a neutral boron hydride which contains one more boron atom than the anionic starting material.

Another object of this invention is to provide a method for the conversion of pentaborane-9 to decaborane-14 and its separation by a sublimation process from the solid reaction medium.

SUMMARY OF THE INVENTION

The preparation of $B_{10}H_{14}$ in high yields in accordance with the method of this invention involves the conversion of pentaborane ($B_5H_9$) to [N(CH$_3$)$_4$][B$_9$H$_{14}$] which is a free-flowing solid under a dry atmosphere at room temperature. A hydride abstraction is completed on the solid by reacting a boron trihalide selected from $BBr_3$ and $BCl_3$ with the solid to yield $B_{10}H_{14}$.

The conversion reaction is accomplished by reacting a 2:1 molar ratio of $B_5H_9$ with NaH in tetrahydrofuran (THF) in the presence of [N(CH$_3$)$_4$][Cl] at room temperature. The THF is subsequently removed from the system and $BCl_3$ or $BBr_3$ is added to the [N(CH$_3$)$_4$][B$_9$H$_{14}$] to form $B_{10}H_{14}$ which is separated from the solid reaction mixture by a sublimation procedure.

BRIEF DESCRIPTION OF THE DRAWING

The FIGURE of the drawing depicts a sublimator unit employed for the removal of $B_{10}H_{14}$ from a laboratory sized reaction vessel.

DESCRIPTION OF THE PREFERRED EMBODIMENTS

The method of this invention provides an efficient procedure for the conversion of pentaborane-9 to decaborane-14. The method is comprised basically of three steps which include:

1. Conversion of $B_5H_9$ to $[N(CH_3)_4][B_9H_{14}]$ by reacting a 2:1 molar ratio of $B_5H_9$ with NaH in tetrahydrofuran (THF) in the presence of $[N(CH_3)_4][Cl]$ at room temperature. $^{11}$B NMR at 32.1 MHz shows the only boron containing species to be $B_9H_{14}^-$.

2. After completion of step 1, THF is removed from the system and $BCl_3$ or $BBr_3$ is added to the solid $[N(CH_3)_4][B_9H_{14}]$ and allowed to react while stirring vigorously at 11° C. to room temperature.

3. After completion of step 2, $B_{10}H_{14}$ is separated by sublimation at 90° C.–110° C. from the solid reaction mixture.

Thus, the treatment of $[N(CH_3)_4][B_9H_{14}]$ with $BCl_3$ gave $B_{10}H_{14}$ in a yield up to about 50% based on $B_9H_{14}^-$ ion.

A reaction (1) is suggested as follows:

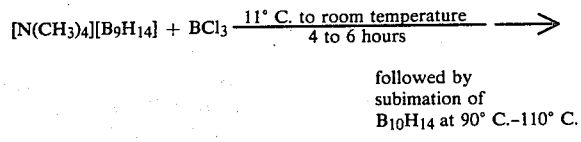

followed by subimation of $B_{10}H_{14}$ at 90° C.–110° C.

$B_{10}H_{14} + [N(CH_3)_4][HBCl_3] + H_2 +$ solid BH residue (1) In this stoichiometry 56% of the boron in $B_9H_{14}^-$, as shown by reaction (1') below which is an abreviated form of reaction (1),

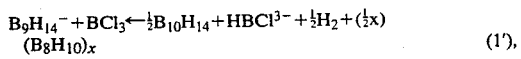

is converted to $B_{10}H_{14}$, which corresponds well with the results described in example below which is close to quantitative.

EXAMPLE—DESCRIPTION OF STEP 1

1. 513 mg NaH (21.4 millimoles), 2.30 g $[(CH_3)_4N][Cl]$ (22 millimoles), and a magnetic stirring bar (1½" long) are placed in a 500 ml roundbottom flask in a dry box using $N_2$ atmosphere. The 500 ml flask is single neck with a 15 mm solv-seal joint glassblown in place of the normal neck opening. A reaction vessel to vacuum line stopcock adapter is attached to the 500 ml flask via this 15 mm solv-seal joint. The adapter is comprised of a 0 to 4 mm bore Kontes Teflon stopcock to which is attached on one side a 15 mm solv-seal joint and on the other side a standard taper 14/35 outer joint.

The reaction vessel (500 ml flask and stopcock adapter) is then removed from the dry box and attached to an inlet port of a standard vacuum line. The reaction vessel is evacuated of dry box $N_2$ and 20 ml of dry THF is condensed into the reaction vessel which is maintained at $-78°$ C. using a dry ice/isopropanol slush. The dry ice/isopropanol slush is then replaced with a liquid $N_2$ Dewar and 4.10 ml $B_5H_9$ (42.8 mmoles), the volume measured at 0° C. where the density of $B_5H_9$ is 0.66 g/cm$^3$ is then condensed into the reaction vessel. The reaction mixture is then warmed to room temperature (26°–27° C.) and is stirred vigorously for 12 hours. Immediate gas evolution is present and continues for several minutes. The solution gradually changes from a clear slurry to light yellow. After 12 hours the reaction vessel is cooled to $-196°$ C. and the $H_2$ produced is measured via a calibrated Toepler pump system. 22 millimoles of $H_2$ is obtained and this corresponds to initial deprotonation of one equivalent of $B_5H_9$ with one equivalent of NaH. The reaction vessel is then warmed to 0° C. while the solvent is removed under vacuum by pumping through a U-trap maintained at $-78°$ C. and a U-trap maintained at $-196°$ C. Total solvent removal takes 3 hours, with the reaction vessel warmed to room temperature after 2 hours. The solid remaining is very light yellow and consists of $[(CH_3)_4N][B_9H_{14}]$ and NaCl. $^{11}$B NMR at 32.1 MHz shows 95% of the boron containing species to be $B_9H_{14}^-$.

EXAMPLE—DESCRIPTION OF STEP 2

20 The $[CH_3)_4N][B_9H_{14}]$ from step 1 is then scraped from the 500 ml reaction vessel and transferred to a similarly equipped 100 ml reaction vessel in the dry box. The stir bar is also transferred. Only a few, <10 mg are lost in the transfer. NOTE: The solid transferred also contains NaCl.

The 100 ml reaction vessel is removed from the dry box, placed on an inlet port of the vacuum line and evacuated of dry box $N_2$. 22.0 mmoles of $BCl_3$ (freed from HCl) measured by gas volume at 26° C. are condensed into the reaction vessel maintained at $-196°$ C. The reaction vessel is then warmed to 11° C. to room temperature ($H_2O$ and small quantity of ice) and stirred.

EXAMPLE—DESCRIPTION OF STEP 3

3. After 4 hours the reaction mixture is cooled to $-196°$ C. and 11 mmoles $H_2$ is removed using the aforementioned Toepler pump system. The reaction vessel is then warmed to room temperature and traces of volatile materials are removed by pumping for a few minutes. The reaction vessel is then removed to the dry box where it is attached to a special "sublimator" for removal of $B_{10}H_{14}$. The "sublimator" system used is depicted in the FIGURE of the drawing and further described below.

The sublimator unit 10 of the drawing is comprised of a bridge U-tube 12 which is shown connected to one end to a reaction vessel 14 in which $B_{10}H_{14}$ is produced in accordance with this invention. The other end of the bridge U-tube is shown attached to one end of the collection U-tube 16. The other end of the collection U-tube 16 is shown connected via a typical 15 mm solv-seal joint 18 to the adapter unit 20 through which a dynamic vacuum is maintained while the collection U-tube 16 is maintained at 0° C. in a $N_2$ Dewar. An oil bath 22 is shown positioned on a magnetic stirrer apparatus 24. The function of the sublimator as employed to remove the $B_{10}H_{14}$ produced in accordance with this invention is described in detail below.

The collection U-tube is maintained at 0° C. while the reaction vessel is slowly warmed to 110° C. The entire sublimator unit is maintained under dynamic vacuum. Decaborane collects slowly in the bridge U-tube and finally in the collection U-tube over a 2-hour period. Initially the $B_{10}H_{14}$ obtained is white but eventually is tinted light yellow by reaction by-products blown through the system due to dynamic vacuum. The amount of impurity is however, quite small (a few milligrams). The initial mass of $B_{10}H_{14}$ obtained is 1.18 g or 45.2% based on $B_5H_9$. This is slightly reduced upon recrystallization which yields much purer $B_{10}H_{14}$ in a 1.10 g quantity or 42.1% yield based on $B_5H_9$ used. The $^{11}B$ NMR of the $B_{10}H_{14}$ shows it to be quite pure.

The detailed description of the distinct three step procedures above are directed to preparing $B_{10}H_{14}$ in 1 gram quantities. It should be recognized that the laboratory method employs glass reactors and vacuum line techniques which are convenient for relatively small scale preparations. Some of the procedures employed in the laboratory method would be obviated in a scale-up procedure in which a metal reactor and metal piping would be employed. Thus, for example, while $B_5H_9$ is condensed into a small glass reactor under vacuum at $-196°$, in a large scale procedure liquid $B_5H_9$ would be forced from its storage cylinder into the metal reactor by $N_2$ gas. In the stage where the mixture of $BCl_3$ and $[N(CH_3)_4][B_9H_{14}]$ is maintained to avoid excessive pressure in the glass reactor, with the metal reactor, room temperature would be permissible. Although vacuum sublimation is used to isolate $B_{10}H_{14}$ in the laboratory method, in the scaled-up procedure a stream of $N_2$ gas could be passed over the subliming $B_{10}H_{14}$ at $110°$ C. and a water-cooled collector would be sufficient to trap the $B_{10}H_{14}$.

In the course of developmental work under Government sponsored research which lead to the conversion of $B_5H_9$ to $B_{10}H_{14}$ by employing a more efficient hydride abstracting agent in accordance with the method of this invention, earlier experiments resulted in some interesting discoveries which will be reported below.

$AlCl_3$ has been found to be useful in the production of $B_{10}H_{14}$ in lower yields (e.g., 23–26%) by an alternate process. For example, earlier experiments indicated that heating the reactants to about $80°$ C. is required so that a reaction melt is formed to provide sufficient contact for subsequent reaction to take place. Generally, reaction between $AlCl_3$ and the borane anions is generally found to be dependent upon formation of a reaction melt from which an immediate reaction ensues upon melting. Several reactant ratios of $AlCl_3$ to produce $B_{10}H_{14}$ by the reaction of $(n-C_4H_9)_4NB_5H_8$ with $AlCl_3$ are summarized in Table I below. With the exception of trial 2, each reaction was conducted at $100°$–$110°$ C. for periods ranging from 14 to 18 hours. Hydrogen was removed by means of a Topler pump until evolution subsided, (approximately 1 hour each case), at which point diffusion pumping was used. The system in trial 2 was evacuated continuously to avoid any pressure build-up. As can be seen, this procedure resulted in a marked decrease in the yield of $B_{10}H_{14}$. However, $B_6H_{10}$ was obtained in greater than average yield, suggesting that this may be an intermediate in the reaction, and a source of $B_{10}H_{14}$ through subsequent pyrolysis which will be discussed in more detail hereinbelow.

The optimum $AlCl_3/(n-C_4H_9H)_4NB_5H_8$ ratio is in the range 3/1 to 2/1 for the highest yields of $B_{10}H_{14}$. Ratios in excess of 3:1 should be avoided due to co-sublimation of excess $AlCl_3$ along with $B_{10}H_{14}$. In such instances it has been possible to separate the aluminum chloride through complexation with diethyl ether.

TABLE I

| | | Reaction of $(n-C_4H_9)_4NB_5H_8$ with $AlCl_3$ | | | | | |
|---|---|---|---|---|---|---|---|
| mmoles (TBA) $B_5H_8$* | | $AlCl_3$ (TBA)$B_5H_8$ | % Yield $B_{10}H_{14}$ | % Yield $B_6H_{10}$ | % Yield $B_5H_9$ | % Yield $B_2H_6$ | % Yield $H_2$ |
| (1) | 4.56 | 1.60 | 13.3 | 1.0 | 14.5 | 3.0 | 21.5 |
| (2) | 8.46 | 1.95 | 4.9+ | 2.4 | 14.4 | 3.2 | — |
| (3) | 8.52 | 2.02 | 23.2 | 1.4 | 4.7 | 3.3 | 16.5 |
| (4) | 10.4 | 2.50 | 21.0 | — | 6.3 | 2.7 | 14.3 |
| (5) | 8.52 | 2.90 | 26.8 | 1.3 | 7.8 | 4.0 | 21.0 |
| (6)** | 10.0 | 3.00 | 22.4 | trace | 10.2 | 4.2 | 11.2 |
| (7) | 8.50 | 3.53 | 25.6 | — | 11.2 | 3.5 | 13.6 |

+System was continuously evacuated which apparently causes a reduced yield of $B_{10}H_{14}$. All other trials in a closed system.
*TBA = $(n-C_4H_9)_4N^+$.
**Trial 6 was conducted at 85° C., all others were run at 100–110° C.

Additional studies of the pyrolysis of $(n-C_4H_9)_4NB_5H_8$ demonstrated that $B_9H_{14}^-$ is a principal product, and is responsible for $B_{10}H_{14}$ production. Another example is the solid $KI/(n-C_4H_9)_4NB_5H_8$ mixture which melts clearly at $85°$ C. without evolution of any volatile species. Reaction of this pyrolysis product, with $AlCl_3$ gives increased yields of $B_{10}H_{14}$. For example, reaction of 0.60 g of the solid $B_5H_8^-$ decomposition product, (corresponding to a boron content of 6.39 mmoles), with 0.50 g, (3.75 mmoles), $AlCl_3$, resulted in a 26.1% yield of $B_{10}H_{14}$. The reaction of $(n-C_4H_9)_4NB_9H_{14}$ with $AlCl_3$ provided conclusive evidence that $B_{10}H_{14}$ is a result of reaction of $B_9H_{14}^-$ with Lewis acids.

A boron trihalide selected from $BBr_3$ or $BCl_3$, because of its volatility and solubility, enables a reaction temperature from about room temperature to about $11°$ C. to be employed in the preferred reactions in accordance with the method of this invention which involves hydride abstraction. Reactions utilizing $BBr_3$ or $BCl_3$ were generally found to proceed at room temperature, and result in uniformly higher yields of $B_{10}H_{14}$ than by similar reactions with $AlCl_3$. Various solvent media such as $CH_2Cl_2$ or pentane may be used; however, the solvent-free reactions which produce high yields of $B_{10}H_{14}$ up to about 50% (based upon total $B_5H_9$ starting material) are preferred.

Because of a substantial inventory of pentaborane ($B_5H_9$) which Government owns as a result of earlier programs to produce high energy boron fuels, the method of this invention should result in savings of many millions of dollars plus ensure an adequate supply of NHC as a result of the practical, relatively simple synthesis of $B_{10}H_{14}$ from $B_5H_9$.

We claim:

1. A method for the preparation of decaborane-14($B_{10}H_{14}$) through the conversion of $B_5H_9$ to $[N(CH_3)_4][B_9H_{14}]$, the hydride ion abstraction reaction of $[N(CH_3)_4][B_9H_{14}]$, by a boron trihalide to form $B_{10}H_{14}$, and the separation and recovery of $B_{10}H_{14}$, in pure form by a sublimation process, said method comprising completing steps (i–IX) as set forth hereinbelow and relating to said conversion, completing steps (X–XIII) as set forth hereinbelow and relating to said hydride ion abstraction reaction, and completing steps (XIV–XV) as set forth hereinbelow and relating to said separation and recovery as follows:

(i) adding to a first reaction vessel provided with a means for stirring and while maintained in a dry box of $N_2$ atmosphere, a predetermined weight of NaH and $[(CH_3)_4N][Cl]$ to provide a 1:1 molar ratio of said NaH and said $[(CH_3)_4N][Cl]$;

(ii) removing said first reaction vessel from said dry box and attaching said first reaction vessel to a vacuum means for removing of dry box $N_2$;

(iii) condensing a predetermined volume of dry tetrahydrofuran into said first reaction vessel maintained at about $-78°$ C. while condensing of said dry tetrahydrofuran into said first reaction vessel to form a reaction mixture;

(iv) subjecting said first reaction vessel and said reaction mixture to a liquid $N_2$ Dewar container for cooling prior to condensing a predetermined volume of $B_5H_9$ measured at $0°$ C. into said reaction mixture, said predetermined volume of said $B_5H_9$ providing a 2 molar ratio of said $B_5H_9$ to said 1:1 molar ratio of said NaH and $[N(CH_3)_4][Cl]$;

(v) warming said first reaction vessel and said reaction mixture to a room temperature of about $26°$ C.$-27°$ C. and stirring said reaction mixture vigorously for about 12 hours to complete a reaction period to form the solid reaction products $[N(CH_3)_4][B_9H_{14}]$ and NaCl in said reaction mixture;

(vi) cooling said first reaction vessel and said solid reaction products to $-196°$ C. and removing hydrogen and other volatiles;

(vii) warming said first reaction vessel and said solid reaction products to about $0°$ C. while removing said solvent under vacuum from said solid reaction products $[N(CH_3)_4][B_9H_{14}]$ and NaCl;

(viii) transferring said solid reaction products to a second reaction vessel in a dry box, said second reaction vessel having a smaller capacity than said first reaction vessel;

(ix) removing said second reaction vessel from dry box and evacuating said second reaction vessel of dry box $N_2$;

(x) condensing a predetermined molar volume of a boron trihalide selected from $BCl_3$ freed from HCl or $BBr_3$ freed from HBr into said second reaction vessel maintained at $-196°$ C., said predetermined molar volume of said boron trihalide being in ratio of 1:2 to said condensed $B_5H_9$;

(xi) warming contents of said second reaction vessel to about $11°$ C. to room temperature and reacting while stirring said contents of said second reaction vessel for a predetermined time period of about 4 hours to form reaction products including $B_{10}H_{14}$ by hydride ion abstraction;

(xii) cooling said second reaction vessel and said reaction products including $B_{10}H_{14}$ and removing hydrogen;

(xiii) warming said second reaction vessel to a room temperature range of about $26°$ C.$-27°$ C. and removing trace of volatile products by vacuum pumping;

(xiv) transferring said second reaction vessel to a dry box; and, (xv) separating said $B_{10}H_{14}$ by sublimation from said second reaction vessel and recovering said $B_{10}H_{14}$ in pure form.

2. The method of claim 1 wherein said boron trihalide selected is $BCl_3$ for completing said reaction in said second reaction vessel and wherein said $B_{10}H_{14}$ is separated from said second reaction vessel by a sublimation process which comprises slowly warming said second reaction vessel and said solid reaction products to about $110°$ C. while said second reaction vessel is connected to a sublimator unit maintained at about $0°$ C. while the entire system of said second reaction vessel and said sublimator unit is maintained under dynamic vacuum.

3. The method of claim 1 wherein said boron trihalide selected is $BBr_3$ for completing said reaction in said second reaction vessel and wherein said $B_{10}H_{14}$ is separated from said second reaction vessel by a sublimation process which comprises slowly warming said second reaction vessel and said solid reaction products to about $110°$ C. while said second reaction vessel is connected to a sublimator unit maintained at about $0°$ C. while the entire system of said second reaction vessel and said sublimator unit is maintained under dynamic vacuum.

4. The method of claim 1 wherein said separation by sublimation employs a stream of $N_2$ gas for passing over the subliming $B_{10}H_{14}$ at $110°$ C. and wherein said $B_{10}H_{14}$ is trapped in a water-cooled collector.

* * * * *